(12) United States Patent
Vancheri

(10) Patent No.: US 12,702,442 B2
(45) Date of Patent: Aug. 11, 2026

(54) DILATOR TIP ASSEMBLY FOR AN ENDOPROSTHETIC DELIVERY DEVICE

(71) Applicant: Bolton Medical, Inc., Sunrise, FL (US)

(72) Inventor: Bryan Vancheri, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 96 days.

(21) Appl. No.: 18/392,762

(22) Filed: Dec. 21, 2023

(65) Prior Publication Data

US 2024/0206912 A1 Jun. 27, 2024

Related U.S. Application Data

(60) Provisional application No. 63/435,101, filed on Dec. 23, 2022.

(51) Int. Cl.

| | |
|---|---|
| ***A61B 17/00*** | (2006.01) |
| ***A61B 17/34*** | (2006.01) |
| ***A61F 2/95*** | (2013.01) |
| ***A61L 31/02*** | (2006.01) |
| ***A61L 31/06*** | (2006.01) |

(52) U.S. Cl.

CPC ...... *A61B 17/3496* (2013.01); *A61B 17/3468* (2013.01); *A61L 31/022* (2013.01); *A61L 31/06* (2013.01); *A61B 2017/00477* (2013.01); *A61B 2017/00526* (2013.01); *A61F 2/95* (2013.01)

(58) Field of Classification Search

CPC ......... A61B 17/11–1155; A61B 17/128–1285; A61B 2017/1103–1157; A61B 2017/1205–12095; A61M 25/001; A61M 25/0009–0015; A61M 25/0067–0084; A61M 25/01–0158; A61M 25/09–104; A61M 2025/0073–0096; A61M 2025/015–0166; A61M 2025/09008–1097; A61F 2/95–97; A61F 2/2427–2439; A61F 2002/9505–9665

See application file for complete search history.

(56) References Cited

U.S. PATENT DOCUMENTS

| | | | | |
|---|---|---|---|---|
| 5,104,025 | A * | 4/1992 | Main .................... | A61B 17/115 227/19 |
| 5,312,360 | A | 5/1994 | Behl | |
| 5,902,333 | A | 5/1999 | Roberts et al. | |
| 7,578,839 | B2 | 8/2009 | Serino et al. | |
| 2008/0009832 | A1 * | 1/2008 | Barron ............... | A61M 39/1011 604/533 |
| 2020/0353212 | A1 | 11/2020 | Holm et al. | |

FOREIGN PATENT DOCUMENTS

| | | |
|---|---|---|
| EP | 1362563 B1 | 11/2003 |

* cited by examiner

*Primary Examiner* — Elizabeth Houston
*Assistant Examiner* — Jonathan A Hollm
(74) *Attorney, Agent, or Firm* — Stephen J. Kenny; Emily H. Yasharpour; Foley Hoag LLP

(57) ABSTRACT

A dilator tip assembly of an endoprosthetic delivery device includes a mounting component of an endoprosthetic delivery device, the dilator tip being mountable on a distal end of the mounting component and defining a luminal conduit having a longitudinal axis and a chamfered proximal end, the luminal conduit including a luminal lateral groove. A circlip mountable on the mounting component at the mounting component lateral groove secures the mounting component to the dilator tip by occupying both the mounting component lateral groove of the mounting component and the luminal lateral groove of the dilator tip.

18 Claims, 9 Drawing Sheets

22
14
26
40
12
42
4B
52
20
54
16
10
28
24
30
22

32
12
56
50
58
18
42
36
34

4C
32
50
42
12
54
52
34
54
16
24
28

4E
4F
10
12
14
16
18
20
22
24
26
28
30
32
34
36
40
41
42
44
50
52
56
58
60

22
14
26
40
26
42
12
16
5B
10
28
30

42
32
36
18
56
32
50
36
12
66
64
28

DILATOR TIP ASSEMBLY FOR AN ENDOPROSTHETIC DELIVERY DEVICE

CROSS-REFERENCE TO RELATED APPLICATIONS

This application claims the benefit of priority to U.S. Provisional Patent Application No. 63/435,101, filed on Dec. 23, 2023. The entire contents of which are hereby incorporated by reference herein.

BACKGROUND OF THE INVENTION

Dilator tips are ubiquitous in endovascular surgery. They are normally fixed at a distal end of a delivery device and are typically cannulated. In use, dilator tips assist in negotiating tortuous vasculature as a prosthetic endovascular device is directed from a point of entry (or "cut down") of the patient, such as a femoral artery, to a surgical site, such as an aortic arch, a descending thoracic aorta, an abdominal aorta, or some other distal point. Typically, the dilator tip assists in guiding the delivery device along a guidewire that previously has been inserted along the path an endoprosthesis is to take to the surgical site. Upon arrival at the surgical site, the delivery device is manipulated to release the endoprosthesis from the delivery device, such as by removing means for fixing the endoprosthesis to the delivery device at proximal and distal ends of the endoprosthesis, and by removing radial constraints to thereby allow or cause radial expansion of the endoprosthesis. Once released from the delivery device the endoprosthesis is retracted, wherein the dilator tip, along with the remainder of the delivery device, is drawn through the endoprosthesis and back through the vasculature along which it was originally delivered.

Generally, a dilator tip is mounted on a distal end of a guidewire catheter or some equivalent component of a delivery device, and secured to the guidewire catheter by threads and/or an adhesive. As a consequence, application of torsional force by the guidewire catheter on the dilator tip during delivery of an endoprosthesis can be translated from the dilator tip to surrounding vasculature, thereby potentially irritating or damaging that vasculature, particularly if that vasculature has been weakened by the procedure or is diseased. Rotational forces on the guidewire catheter may be necessary to properly orient the endoprosthesis prior to release from the delivery device, making axial rotation of the dilator tip an inherent risk to the patient, depending upon the delivery procedure and the type of endoprosthesis.

Therefore, a need exists for a dilator tip and a dilator tip assembly, as appropriate, that overcomes or minimizes the above referenced problems.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

The present disclosure is generally directed to a dilator tip assembly for an endoprosthetic delivery device that facilitates navigation of vasculature to deliver an endoprosthesis to a surgical site.

In one embodiment, a removable dilator tip assembly of an endoprosthetic device of the present disclosure includes a mounting component, the mounting component including a proximal end and a distal end, and defining a mounting component lateral groove between the proximal end and the distal end. A dilator tip of the endoprosthetic device is mountable on the distal end of the mounting component, wherein the dilator tip has a proximal end and a distal end, and defining a luminal conduit having a chamfered proximal end, and wherein the luminal conduit includes a luminal lateral groove between the proximal end and the distal end of the luminal conduit. A circlip (also known as a snap ring, C-clip, rotor clip, or Jesus clip) is mountable on the mounting component at the mounting component lateral groove, wherein longitudinal travel of the circlip, while mounted on the mounting component lateral groove, along the chamfered proximal end toward the luminal conduit causes radial compression of the circlip, whereby the circlip is directed to the luminal lateral groove and expands within the luminal groove, aligning with and engaging the luminal lateral groove, and securing the dilator tip to the mounting component, the dilator tip thereby being mounted on the mounting component.

In various embodiments, the mounting component of the dilator tip assembly of the present disclosure includes a threaded portion at the distal end that threadably engages the threads of the luminal conduit, and the mounting component lateral groove is proximal to the threaded portion of the mounting component, whereby the mounting component can be removed from the dilator tip by axial rotation of either the mounting component or the dilator tip to thereby disengage the threaded portion of the mounting component from the threads of the luminal conduit.

In various embodiments, the present disclosure is directed to a method of mounting a dilator tip to a mounting component of an endoprosthetic delivery device including the step of assembling a circlip with a mounting component of an endoprosthetic delivery device at a mounting component lateral groove defined by the mounting component and located between a proximal end and a distal end of the mounting component. The distal end of the mounting component, while assembled with the circlip, is directed into a chamfered proximal end of a luminal conduit of a dilator tip of the endoprosthetic delivery device, whereby the circlip is radially compressed during travel in a distal direction along the chamfered proximal end, further travel of the circlip into the luminal conduit of the dilator causing the circlip to be directed into and expand within a luminal groove defined by the luminal conduit, thereby mounting the dilator tip on the mounting component.

This present disclosure has several advantages. For example, the circlip of the dilator assembly, when engaged with the mounting component lateral groove of the mounting component and the luminal lateral groove of the dilator tip, secures the dilator tip to the mounting component without the risk of failure and accidental loss of the dilator tip from the mounting component, such as by failure of an adhesive that would otherwise secure the dilator tip to the mounting component. Further, in various embodiments, where the mounting component and the dilator tip are not threadably engaged, the circlip permits axial rotation of the dilator tip relative to the mounting component, thereby preventing application of torsional force by the mounting component on the dilator tip, or torsional force of the dilator tip on the mounting component. Further, in various embodiments wherein the dilator tip and the mounting component are threadably engaged, and where the luminal conduit includes a chamfered proximal end, the dilator tip can be selectively disengaged from the mounting component by axially rotating the mounting component relative to the dilator tip to thereby cause leveraged retraction of the mounting component to force travel of the circlip longitudinally across the luminal chamfered proximal end of the luminal lateral groove, thereby compressing the circlip and causing subsequent travel of the circlip along the luminal conduit during retraction of the mounting component from the luminal conduit and to remove the dilator tip from the mounting component. As a consequence, the dilator tip can be removed selectively from the mounting component by axial rotation of the mounting component relative to the dilator tip outside the patient, such as during a demonstration of the dilator tip assembly of the present disclosure.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

Figures 1A, 1B, 1C:
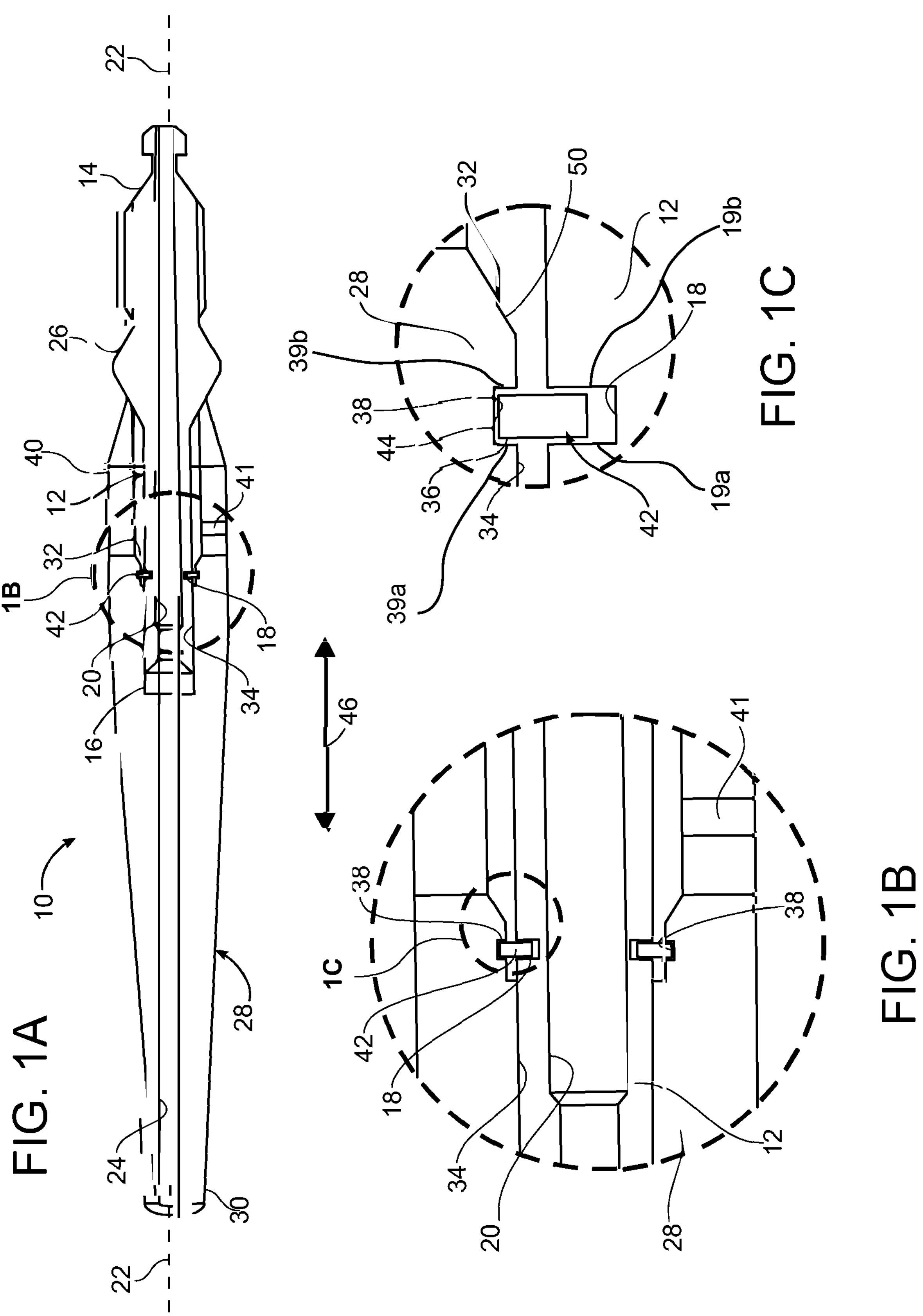
FIG. 1A is one embodiment of a dilator tip assembly of an endoprosthetic delivery device of the present disclosure shown in cross section.
FIG. 1B is a detail of the dilator tip assembly shown in FIG. 1A.
FIG. 1C is a detail of a circlip, in this embodiment, an E-clip, securing a dilator tip to a mounting component, as shown in FIGS. 1A and 1B.

The foregoing will be apparent from the following more particular description of example embodiments of the present disclosure, as illustrated in the accompanying drawings in which like reference characters refer to the same parts throughout the different views. The same number in different drawings represents the same item. The drawings are not necessarily to scale, emphasis instead being placed upon illustrating embodiments of the present disclosure.

DETAILED DESCRIPTION OF THE INVENTION

Reference will now be made in detail to exemplary embodiments of the disclosed subject matter, an example of which is illustrated in the accompanying drawings. The method and corresponding steps of the disclosed subject matter will be described in conjunction with the detailed description of the system.

The features and other details of the present disclosure, either as steps of the present disclosure or as combinations of parts of the present disclosure will now be more particularly described and pointed out in the claims. It will be understood that the particular embodiments of the present disclosure are shown by way of illustration and not as limitations of the present disclosure. The principle features of this present disclosure can be employed in various embodiments without departing from the scope of the present disclosure.

The present disclosure generally is directed to a dilator tip assembly of an endoprosthetic delivery device. The dilator tip assembly can be securely mounted on an endoprosthetic delivery device, either during assembly prior to surgical implementation of an endoprosthesis, or during demonstration of the device apart from surgery. In various embodiments, a dilator tip component of the dilator tip assembly can be separated from the remainder of the endoprosthetic delivery system.

In one embodiment of the present disclosure, shown in cross-section in FIG. 1A, endoprosthetic delivery device 10 includes mounting component 12, having proximal end 14 and distal end 16, and defining mounting component lateral groove 18 between proximal end 14 and distal end 16. Mounting component 12 defines conduit 20 that, in various embodiments, can be longitudinally aligned along longitudinal axis 22 with, or integral, to guidewire catheter 24, through a guidewire (not shown) can extend. In one embodiment, mounting component 12 extends through distal capture component 26 of an apex clasp assembly (the remainder of which is not shown). Mounting component 12 is formed of the suitable material as is known in the art, such as at least one member of the group consisting of 303 stainless steel and polyether ether ketone. A suitable example of an apex clasp assembly is described in WO 2021/262264, the teachings of which are incorporated by reference in their entirety.

Dilator tip 28 of endoprosthetic delivery device 10 is mountable on, and in some embodiments circumscribes, distal end 16 of mounting component 12 and, as shown in FIG. 1A is mounted on distal end 16 of mounting component 12. In some embodiments, the dilator tip 28 and mounting component 12 are coupled in an overlapping fashion, with a proximal end of the dilator tip 28 located proximal to the distal end 16 of the mounting component 12; but with the proximal end 14 of the mounting component located proximal with respect to the proximal end of the dilator tip 28. The mounting component 12 can be positioned (at least partially) within the dilator tip 28, with the mounting component 12 inserted a sufficient distance within the dilator tip such that the lateral groove 18 is located within the dilator tip 28.

Dilator tip 28 has distal end 30 and chamfered proximal end 32 on the internal surface or diameter. Chamfered, as disclosed herein, can mean a rounded/non-planar surface; or alternatively a planar surface that forms an acute angle with respect to the horizontal/longitudinal direction. In other words, "chamfered" can mean a structure that does not form an abrupt, right angle between two surfaces. The chamfered proximal end 32 is positioned internal surface (e.g. facing the mounting component to be inserted therein) and is located at position between he distal and proximal ends of the dilator tip (e.g. as shown in FIG. 1A, the chamfered proximal end 32 is located closer to the proximal end of dilator tip 28 than the distal end).

As can be seen in FIG. 1A, in one embodiment, dilator tip 28 is tapered at distal end 30. Dilator tip 28 defines luminal conduit 34 extending along longitudinal axis 22. Luminal conduit 34 can be configured with a greater diameter than guidewire catheter 24, and extend to a location distal of the mounting component 12. Luminal conduit 34 defines luminal lateral groove 36 between distal end 30 and chamfered proximal end 32 of dilator tip 28; in the exemplary embodiment shown the luminal lateral groove 36 is located closer to the chamfered proximal end 32 than the distal end 30 of the dilator tip 28.

The luminal lateral groove 36 can be formed from a larger diameter than luminal conduit 34; e.g. the dilator tip 28 and mounting component 12 can have axially aligned and corresponding notches or cut-outs in their respective structure to define the luminal lateral groove 36. In some embodiments, the depth/distance the luminal lateral groove 36 extends into the mounting component 12 is greater than the depth/distance the luminal lateral groove 36 extends into the dilator tip 28, as shown in FIG. 1C. Peripheral (or "upper" as shown in FIG. 1C) surfaces 38 and sidewalls 39*a,b* of luminal lateral groove 36 are defined by dilator tip 28; with surfaces 18 and sidewalls 19*a,b* of the luminal lateral groove 36 defined by the mounting component 12. In the exemplary embodiment shown in FIG. 1C, the walls defining luminal lateral groove 36, e.g. walls 38 and 18, are planar walls with a perpendicular configuration relative to the adjacent walls, however alternative geometries (e.g. curvilinear surfaces, angled wall junctures, etc.) are to be considered within the scope of the present disclosure. Dilator tip 28 is formed of a suitable material as is known in the art, such as an aromatic ether-based polyurethane.

In various embodiments, outer component 40 is present and fixed to chamfered proximal end 32 of dilator tip 28. The outer component can be positioned proximal of the chamfered end 32 and have an inner diameter equivalent to the reduced/smaller diameter of the chamfered end 32. In other words, the inner diameter of conduit 34 can increase as it crosses the chamfered end 32 of the dilator tip 28. If present, outer component can, in one embodiment, define flush port 41 which is in fluid communication with the luminal conduit 34. The flush port 41 located proximal to the chamfered end 32 of the dilator tip 28 and luminal lateral groove 36.

Circlip 42 of endoprosthetic delivery device 10 is mountable on mounting component 12 at mounting component lateral groove 18 and defines edge 44. As shown in FIG. 1A, circlip 42 is mounted on mounting component 12 at, or within, mounting component lateral groove 18. As shown in FIG. 1B-1C, circlip 42 occupies at least a portion of mounting component lateral groove 18 of mounting component 12 and luminal lateral groove 36 of dilator tip 28, thereby preventing longitudinal movement of dilator tip 28 relative to mounting component 12. That is, the vertical walls of the clip 42, upon application of a longitudinal force, advance to abut the vertical walls 19*a, b* and 39*a,b* of the luminal lateral groove 36, thereby securing dilator tip 28 to mounting component 12. Relative longitudinal movement of mounting component 12 and dilator tip 28 is indicated by arrow 46.

As can be seen in FIG. 1C, circlip 42, in one embodiment of the present disclosure, the circumferential outer edge 44 of circlip 42 rests against peripheral surface 38 of luminal lateral groove 36, whereby circlip 42 is under radial compression while at least partially occupying luminal lateral groove 36. The luminal lateral groove 36 can be sized such that its dimensions (e.g. radial depth) is greater than at least some portion of the circlip 42, as shown in FIG. 1C.

Figures 1D, 1E, 1F:
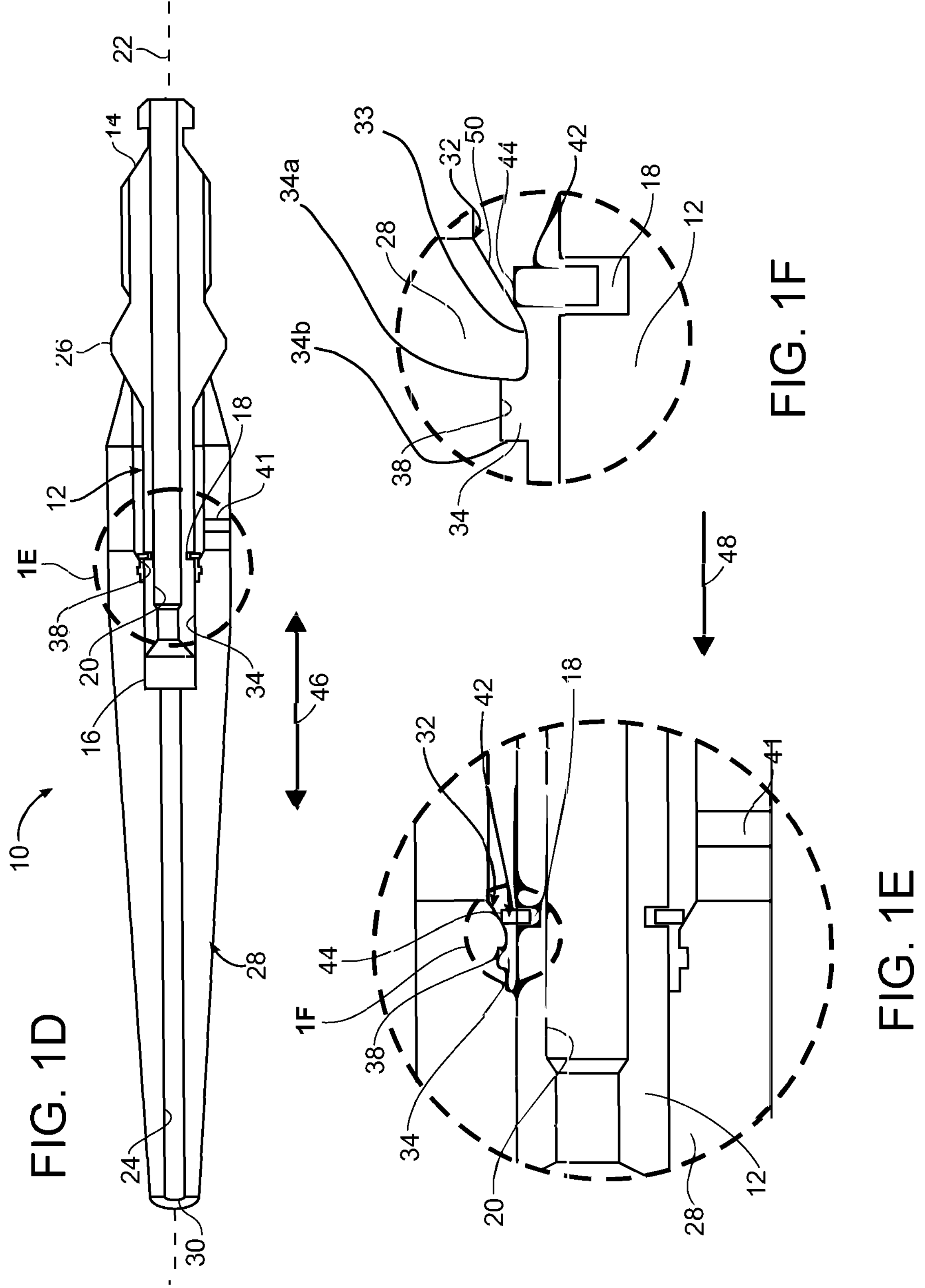
FIG. 1D is another view of the embodiment of the present disclosure shown in FIG. 1A, but while the dilator tip is being mounted on a distal end of the mounting component of the dilator tip assembly of the present disclosure.
FIG. 1E is a detail of FIG. 1D while the E-clip while being compressed.
FIG. 1F is a detail of FIG. 1E showing distal longitudinal travel of the E-clip along a chamfered proximal end of a luminal conduit of the dilator tip

FIGS. 1D-1F show a spatial relationship between mounting component 12 and dilator tip 28 while mounting dilator tip 28 is coupled to mounting component 12. As can be seen in FIG. 1D, circlip 42 is mounted on mounting component 12 at lateral groove 18, but does not, at this stage of the assembly, occupy any portion of luminal lateral groove 36 defined by luminal conduit 34 of dilator tip 28. In the position shown in FIG. 1F, the luminal lateral groove 38 is spaced distally from the circlip 42.

As can be seen in FIG. 1E, and even more clearly in FIG. 1F, circlip 42 is partially radially compressed (see FIG. 2A, described infra) as it travels distally relative to dilator tip 28 along chamfered proximal end 32 in direction of arrow 48. It is noted that these figures depict cross sectional views with the circlip shown as having a rectangular cross section with planar sides, though additional/alternative shapes and sizes are within the scope of the present disclosure. For example, the circlip 42 can also have chamfered or rounded edges to: increase surface area contact with the dilator tip surface 50, and/or reduce the likelihood of a sharp edge of the circlip from breaking off or damaging the dilator tip surface 50.

As mounting component 12 and circlip 42 continue to move longitudinally in distal direction of arrow 48 relative to distal tip 28, circlip 42 continues to advance and slide along the angled face 50 of the chamfered proximal end 32 and becomes further radially compressed until it is sufficiently radially compressed to travel longitudinally within luminal conduit 34. That is, the circlip 42 is radially compressed to a diameter small enough to fit within the luminal conduit 34, with its top surface 44 positioned below surface 33 of the dilator tip 28, as shown in FIG. 1F. Circlip 42 continues to move distally in longitudinal direction of arrow 48 within luminal conduit 34 until it reaches luminal lateral groove 36 (formed in the dilator tip 28), at which point the circlip 42 expands until edge 44 of circlip 42 abuts peripheral surface 38 of luminal lateral groove 36, as can be seen in FIG. 1C, thereby securing distal tip 28 to mounting component 12.

In various embodiments, circlip 42, when fully expanded and at least partially occupying luminal lateral groove 36, does not abut peripheral surface 38 of luminal lateral groove 36. In some embodiments, only select (e.g. thicker/wider) portions of circlip 42 abut the interior walls/surfaces of grooves 36 and 18. Regardless of whether circlip 42 abuts peripheral surface 38 of luminal lateral groove 36, dilator tip 28 can freely axially rotate about longitudinal axis 22 relative to mounting component 12. The distal and proximal edges/sides of circlip are retained within the boundaries formed by the sidewalls 34*a*, 34*b* which form the luminal lateral groove 36. These sidewalls 34*a,b* inhibit/prohibit further longitudinal movement between the mounting component 12 and dilator tip 28.

In operation, the mounting component lateral groove 18, and the luminal lateral groove 36 are recesses in the mounting component 12 and dilator tip 28, respectively. The mounting component lateral groove 18 is initially located distal to the luminal lateral groove 36. As the two grooves 18,36 are brought closer together (either, or both, components 12 and 28 can be moved relative to the other) the two grooves 18, 36 are brought into alignment such that their partial recesses now combine to define a larger channel (which holds the circlip 42 therein).

Figures 2A, 2B:
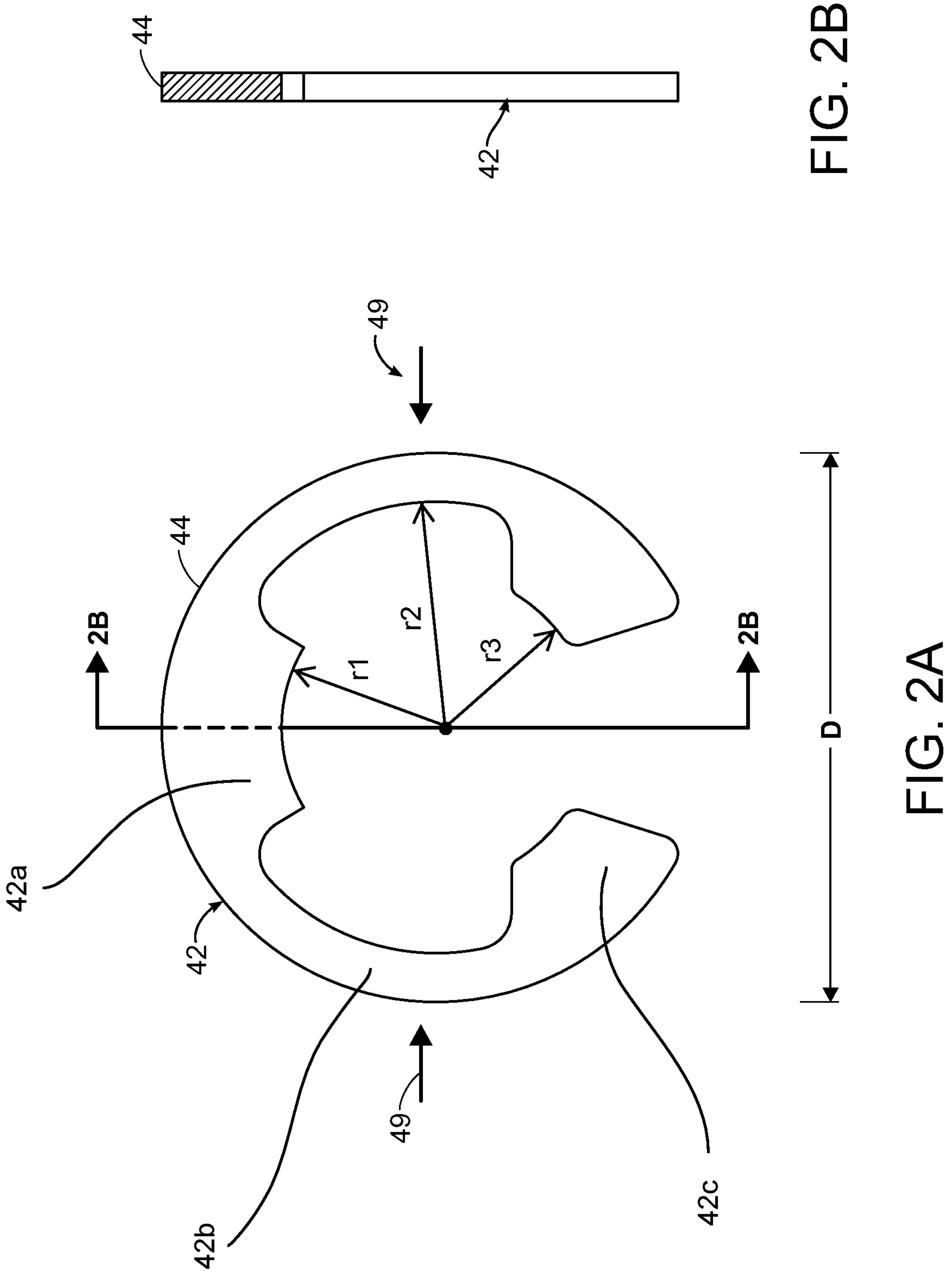
FIG. 2A is a plan view of an embodiment of a suitable circlip for use with the dilator tip assembly of the present disclosure, wherein the circlip is an E-clip.
FIG. 2B is a cross-sectional view of the E-clip shown in FIG. 2A, taken along lines 2B-2B.

Circlip, also known as a "c-clip," "rotor clip," "snap ring," or "Jesus clip," can take various forms, shapes and sizes. FIG. 2A is a plan view of one embodiment of circlip 42, specifically, in this embodiment, an "E-clip," with two protruding legs and a midsection which protrudes a lesser distance than the legs, and is suitable for use in the present disclosure. FIG. 2B is a cross-sectional view of FIG. 2A, taken along line 2B-2B. E-clip of FIGS. 2A and 2B show edge 44. Circlip 42 is fabricated of a suitable material as is known in the art, such as at least 250 ksi 300 series stainless steel. The circlip can have a symmetrical design or asymmetrical design.

In the embodiments shown in FIGS. 2A-B, the circlip can have a non-uniform (radial) thickness 42*a*, 42*b*, 42*c*, with the middle portion 42*b* having the smallest thickness. The circlip 42 can also include arcuate radially interior surfaces. The arcuate radial surfaces can have uniform, or varying, radii of curvature. In the embodiment shown, the circlip has three distinct radii of curvature, with radius r1 forming a first radially interior surface corresponding with thickness 42*a*; radius r2 forming a second radially interior surface corresponding with thickness 42*b*, radius r3 forming a third radially interior surface corresponding with thickness 42*c*. In some embodiments radii r1 and r3 can be equivalent. The thinner section 42*b* serve as spring members which permit the radial compression (in the direction of arrow 49) of the circlip as it is longitudinally advanced in direction 48 and engages the chamfered surface 50 of the dilator tip 28. Then, once advanced to be positioned within the luminal lateral groove 38, the circlip legs 42*b* spring back to original diameter size, and are retained within the groove 38. Thus, the circlip 42 is, in the initial loading position, mounted only to lateral groove 18 of the mounting clip 12; the circlip is then moved longitudinally (and compressed due the chamfered surface 50) into the groove 36 of the dilator tip 28.

Figure 3A:
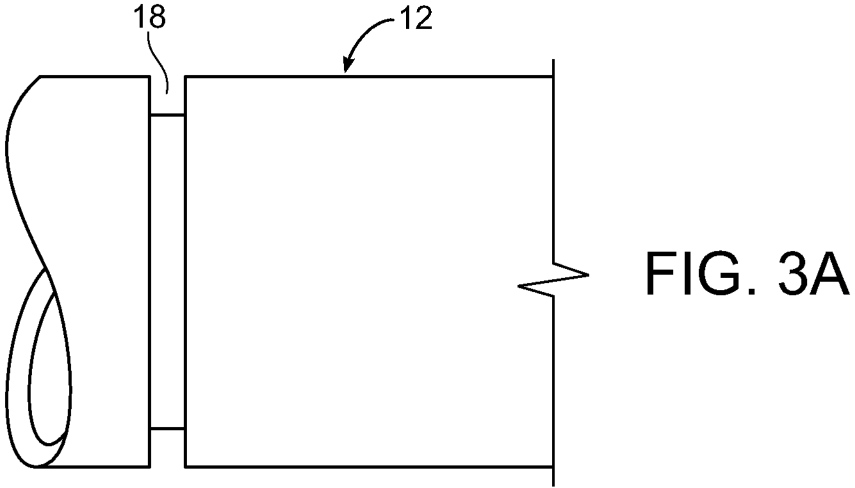
FIG. 3A is a side view of a mounting component of a dilator tip assembly of the present disclosure, showing a mounting component lateral groove defined by the mounting component.

FIG. 3A is a side view of a portion of mounting component 12 represented in FIGS. 1A-1F, showing mounting component lateral groove 18 defined by mounting component 12, between proximal end 14 and distal end 16 of mounting component 12. Groove 18 has a smaller outer diameter than the remainder of component 12. Additionally or alternatively, the groove 18 can extend around the entire circumferential surface of component 12 in some embodiments (so as to not circumscribe the component), and/or extend around only a portion of the circumferential surface of component 12 (so as to not circumscribe the component).

Figure 3B:
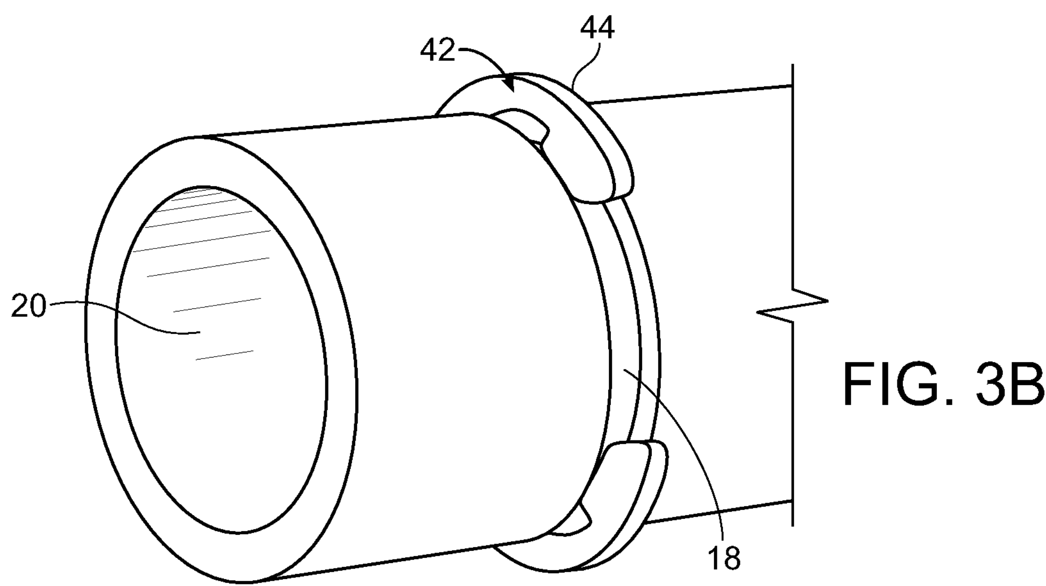
FIG. 3B is a perspective view of the mounting component and mounting component lateral groove shown in FIG. 3A, with a circlip, in this embodiment an E-clip, mounted at the mounting component lateral groove.

FIG. 3B is a perspective view of mounting component 12 and circlip 42 mounted on mounting component 12 at mounting component lateral groove 18 shown in FIG. 3A. Radial compression of circlip 42 reduces the diameter D of circlip, as represented by arrow 49, shown in FIG. 2, described supra. In the exemplary embodiment shown, the longitudinal thickness of the circlip 42 is approximately equivalent to the size of the groove 18, however the groove 18 can be formed with a wider/larger dimension to facilitate placement/reception of the circlip 42 within the groove 18.

In one embodiment, a method of securing dilator tip 28 to mounting component 12 of endoprosthetic delivery device 10 of the present disclosure includes the step of assembling circlip 42, such as that shown in FIGS. 2A and 2B, with mounting component 12, such as shown in FIGS. 3A and 3B of endoprosthetic delivery device 10, such as shown in FIGS. 1A through 1C, at mounting component lateral groove 18, shown in FIG. 3B, wherein, as shown in FIGS. 1A through 1C, mounting component lateral groove 18 is between proximal end 14 and distal end 16 of mounting component 12. Distal end 16 of mounting component 12, while assembled with circlip 42, as shown in FIG. 3B, is directed into luminal conduit at chamfered proximal end 32 of luminal conduit 34, as shown in FIGS. 1D through 1F. As can be seen most clearly in FIGS. 1E and 1F, wherein proximal end of luminal conduit 34 includes chamfered proximal end 32 defined by chamfered surface 50, shown FIG. 1F, distal travel of circlip 42 relative to dilator tip 28 in a longitudinal direction, indicated by arrow 48, causes circlip 42 to be radially compressed as shown by arrows 49 of FIG. 2A-B, from a first diameter to a second diameter. Further travel of circlip 42 into luminal conduit 34 of dilator tip 28 following radial compression of circlip 42 by distal travel along chamfered surface 50 of chamfered proximal end 32, causes circlip 42 to be directed into and expand within luminal lateral groove 36 defined by luminal conduit 34, as shown in FIGS. 1A through 1C, thereby securing dilator tip 28 to mounting component 12.

Figures 4A, 4B, 4C:
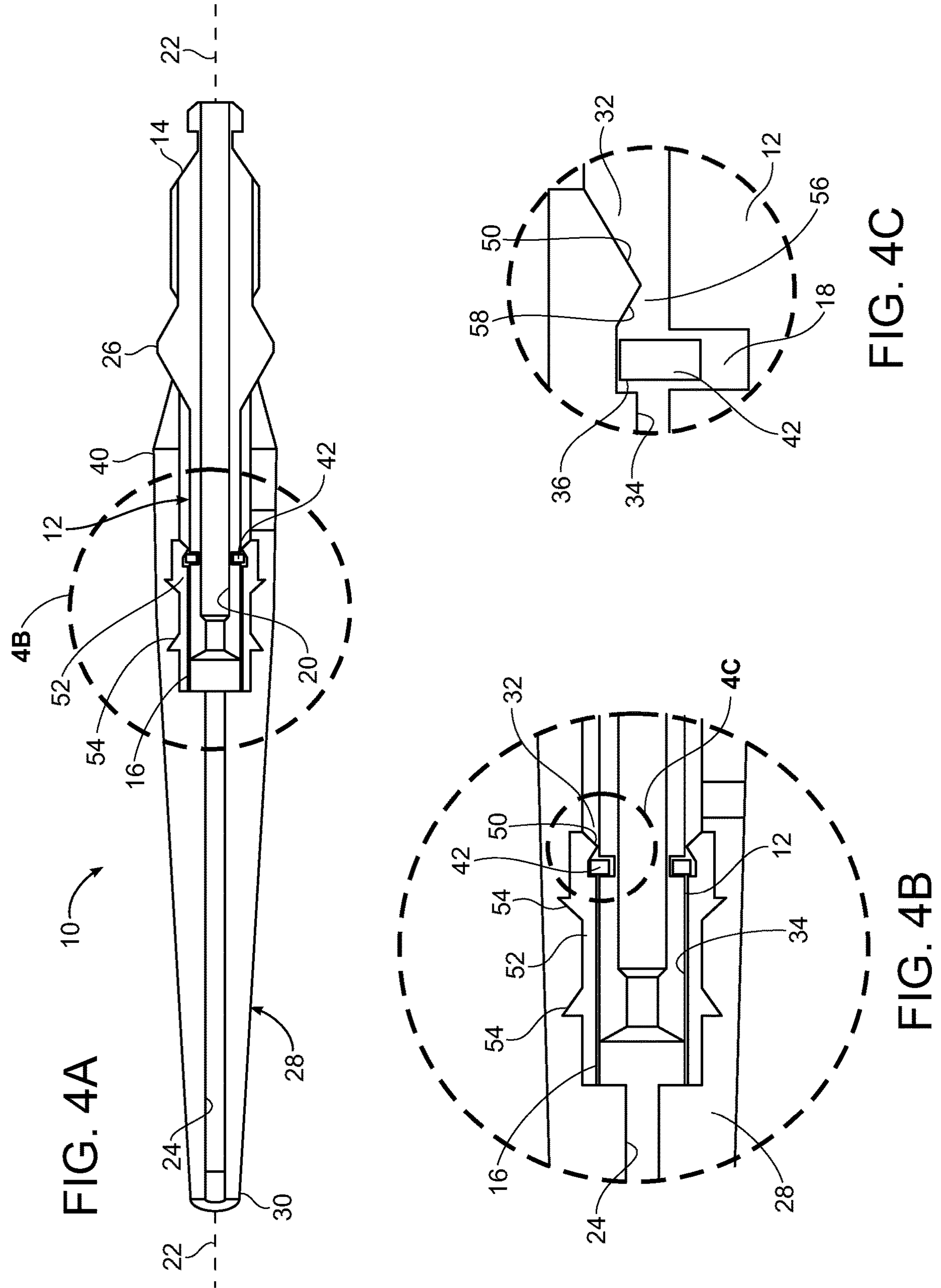
FIG. 4A is a cross-sectional view of an embodiment of a dilator tip assembly of the present disclosure, wherein the dilator tip includes an insert, and wherein, in various embodiments, the proximal end of the luminal conduit of the dilator tip is chamfered.
FIG. 4B is a detail of the insert of the dilator tip while the dilator tip is secured to the mounting component by a circlip which is, in this embodiment, an E-clip.
FIG. 4C is a detail of the E-clip in the luminal conduit of the dilator tip and the mounting component lateral groove, thereby securing the dilator tip to the mounting component, and wherein the proximal end of the luminal conduit is chamfered.

FIGS. 4A-4F represent an alternative embodiment of the dilator tip assembly of the present disclosure. As can be seen in FIG. 4A, in this embodiment of the present disclosure, dilator tip 28 includes insert 52, wherein insert 52 defines luminal lateral groove 36. Insert 52 can be formed of a suitable material such as, for example, at least one material selected from the group consisting of 303 stainless steel and 17-4PH stainless steel. Insert 52 can be formed as a discrete component and attached to remainder of dilator tip 28 by a suitable means, such as by an interference fit, adhesion, welding, etc. between insert 52 and remainder of dilator tip 28.

In some embodiments, the insert 52 can include retention features such as prongs 54 which extend radially outward from the insert 52. The retention features 54 can circumscribe the insert 52, as shown by their depiction on the upper and lower sides of the cross sectional view in FIG. 4B. These retention features can form a mechanical coupling (e.g. tongue and groove fitting) with complimentary surface(s) of the dilator tip so as to mate the insert 52 to the dilator tip 28 and inhibit/prohibit relative movement between these components. In the exemplary embodiment shown a first prong 54 is located near the proximal end of the insert with an upwardly extending ramp/buttress shape that abuts the dilator tip 28 to prevent proximal movement of the insert relative to the dilator tip 28. Additionally, a second prong 54 is located near the distal end of the insert with an upwardly extending ramp/buttress shape that abuts the dilator tip 28 to prevent distal movement of the insert relative to the dilator tip 28. The retention features 54 are located distal to the groove 18 and circlip 42, as shown in FIG. 4A-C.

Figures 4D, 4E, 4F:
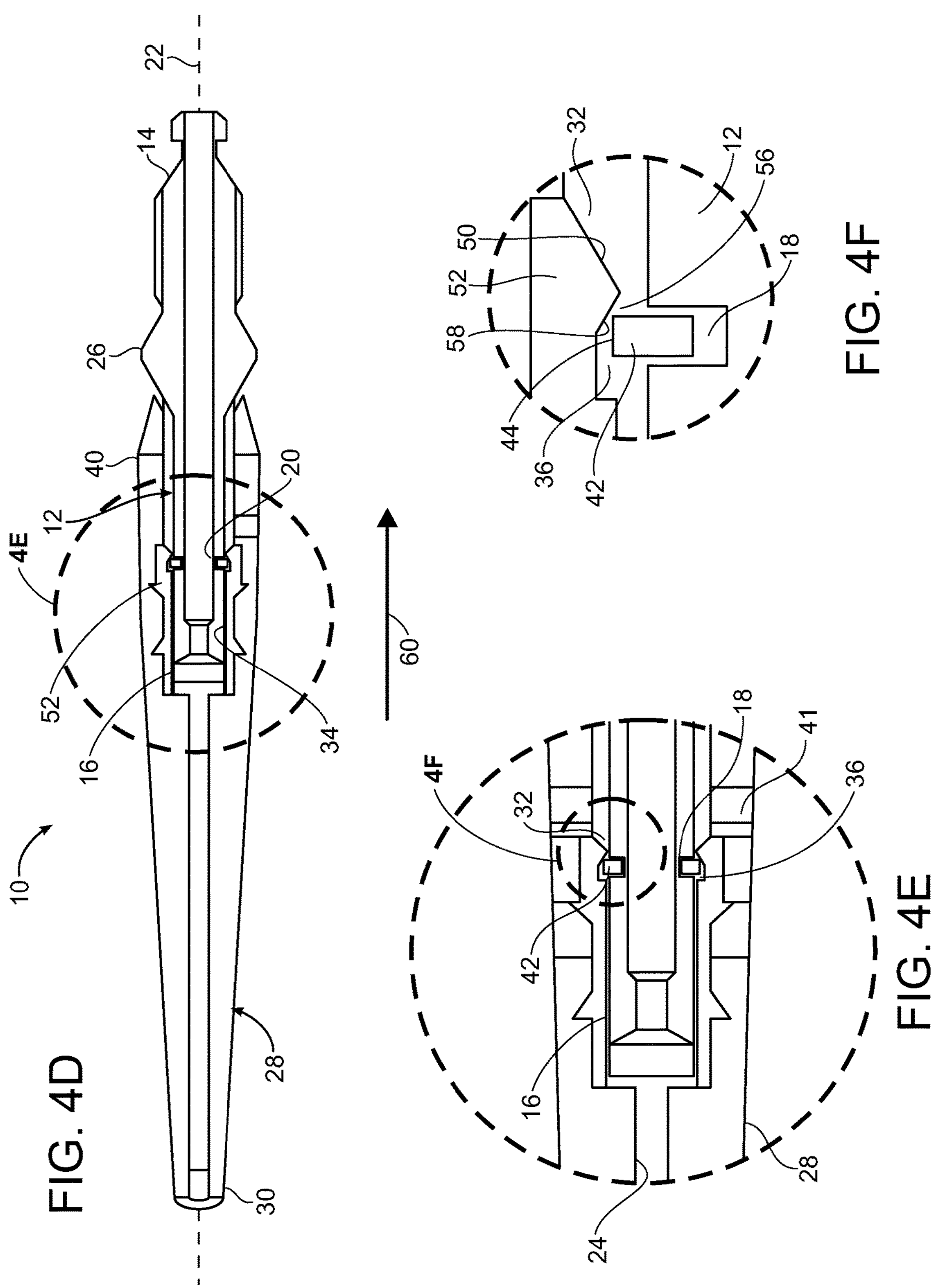
FIG. 4D is a detail of FIG. 4A, but wherein the E-clip is partially collapsed as it travels longitudinally in a proximal direction prior to release of the dilator tip from the mounting component.
FIG. 4E is a detail of FIG. 4D, wherein the E-clip is partially compressed during removal of the dilator tip from the mounting component.
FIG. 4F is a detail of FIG. 4E, showing radial compression of the E-clip as it travels longitudinally in a proximal direction along the luminal chamfered proximal end of the luminal lateral groove of the dilator tip prior to dismounting, or release of, the dilator tip from the mounting component.

The remainder of the components of the embodiment of FIGS. 4A through 4F are similar to and incorporate the functionality described above with respect to FIGS. 1A through 1C, however, in this exemplary embodiment a proximal end of luminal lateral groove 36 of luminal conduit 34 is chamfered. In the exemplary embodiment illustrated in FIGS. 4A-F, a chamfered luminal proximal end 56 is defined by luminal lateral groove proximal chamfered surface 58. In this embodiment, proximal longitudinal travel in direction of arrow 60 of mounting component 12 relative to dilator tip 28 causes circlip 42 to radially compress, as shown in FIGS. 4D-4F. It is to be understood, however, that the embodiment of FIGS. 4A-4F, wherein dilator tip 28 includes insert 52, need not include chamfered proximal end 56 of luminal lateral groove 36, but instead include luminal lateral groove 36 as shown in FIGS. 1A-IF, wherein the proximal end is not chamfered, but, rather is normal to luminal conduit 34, as shown in FIGS. 1A-1F. As in the embodiment shown in FIGS. 1A-IF, dilator tip 28 of the embodiment shown in FIGS. 4A-4F can freely rotate axially about longitudinal axis 22 relative to mounting component 12.

As can be seen in each of FIGS. 4D through 4F, during retraction from luminal conduit 34 of dilator tip 28, edge 44 of circlip 42 travels longitudinally in distal direction of arrow 60 along lateral groove proximal chamfered surface 58 of luminal lateral groove 36 as mounting component 12, thereby radially compressing circlip 42 until edge 44 of circlip 42 traverses chamfered proximal end 56 of luminal lateral groove 36. Further retraction of mounting component 12 from luminal conduit 34 of dilator tip 28 allows circlip 42 to expand as edge 44 travels proximally across chamfered surface 50 defining chamfered proximal end 32 of luminal conduit 34, as shown in FIGS. 1D-1F, described supra. After traversal of circlip 42 across chamfered proximal end 56 of luminal lateral groove 36, and expansion of circlip 42 by travel along chamfered surface 50 of chamfered proximal end 32 of luminal conduit 34 of dilator tip 28, mounting component 28 is released from dilator tip 28 or, viewed conversely, dilator tip 28 is dismounted, or disassembled from mounting component 12.

Figures 5A, 5B:
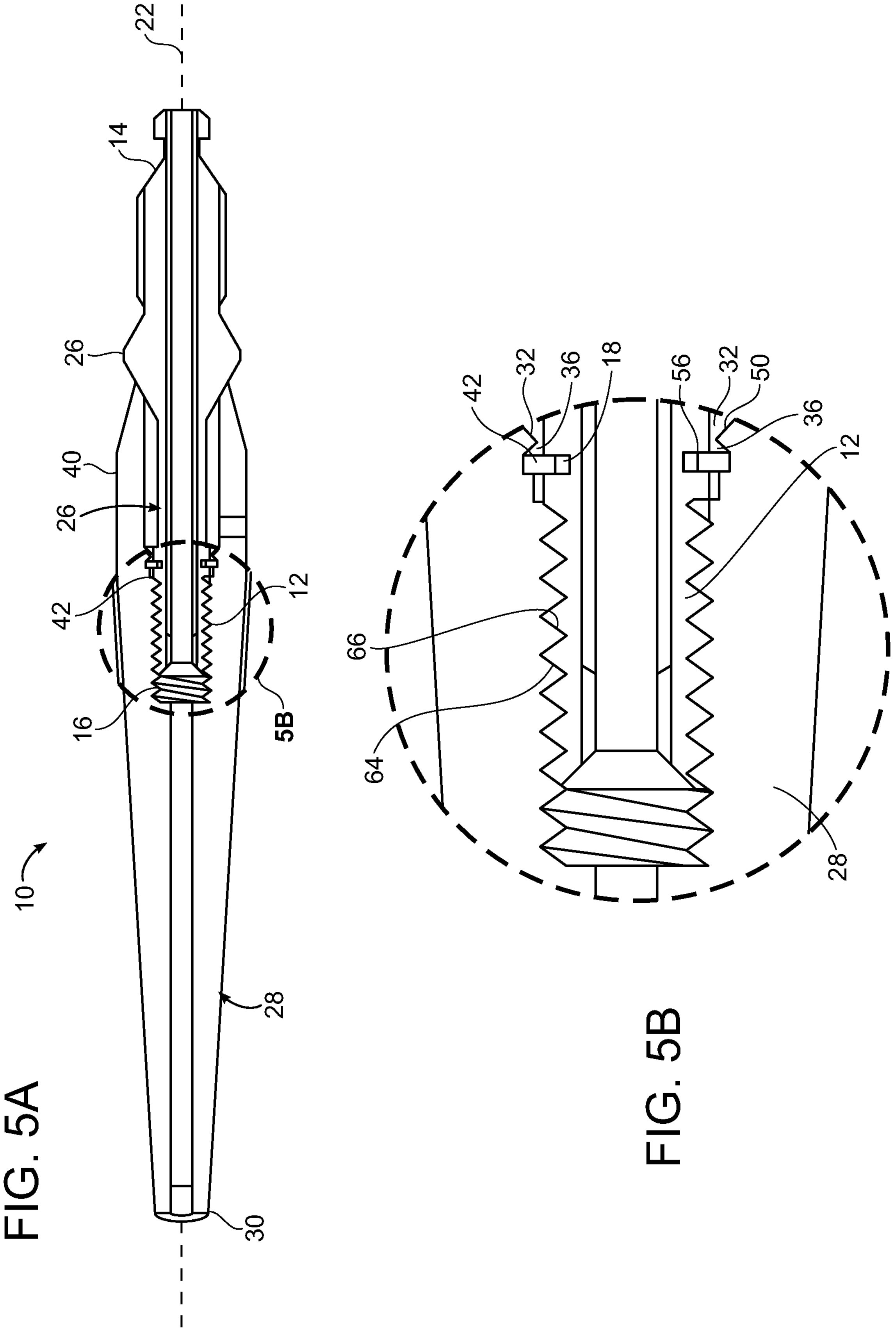
FIG. 5A is a cross-sectional view of another embodiment of the dilator tip assembly of the present disclosure, wherein the mounting component and the dilator tip are threadably engaged, and wherein the dilator tip is secured to the mounting component by a circlip, which in this embodiment is an E-clip.
FIG. 5B is a detail of the threaded engagement of the mounting component and dilator tip of FIG. 5B.
Figures 5C, 5D:
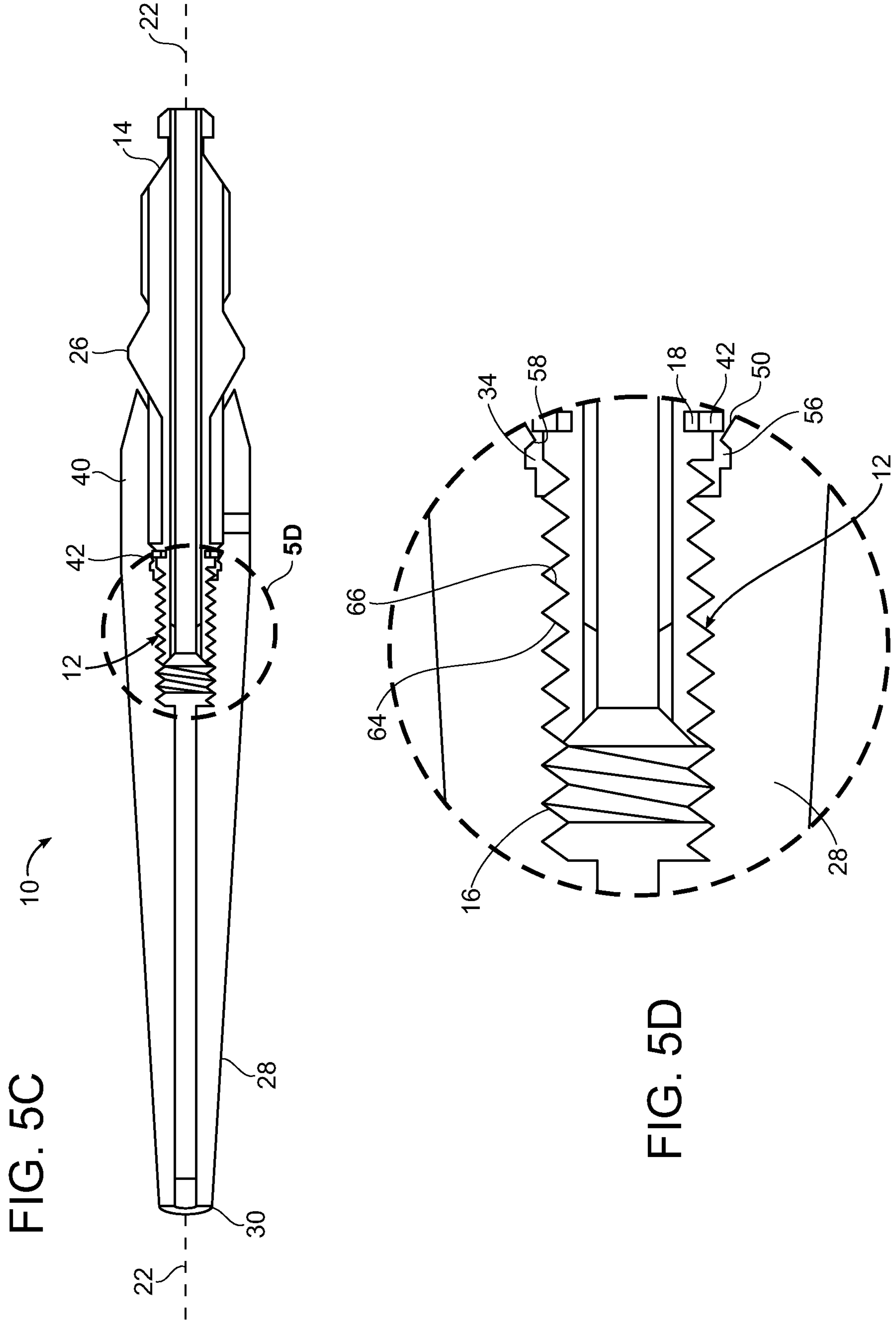
FIG. 5C is a representation of the dilator tip assembly of FIG. 5A, but wherein the dilator tip is only partially threaded onto the mounting component, and the E-clip is traveling longitudinally along the chamfered proximal end of the luminal conduit.
FIG. 5D is a detail of FIG. 5C.

In yet another embodiment of dilator tip assembly of the present disclosure, shown in FIGS. 5A through 5D, mounting component 12 includes threaded portion 62 at distal end 16, wherein mounting component lateral groove 18 is proximal to threaded portion 62 of mounting component 12. As shown in FIGS. 5A and 5B, in addition to chamfered proximal end 32 of luminal conduit 34, dilator tip 28 can, in various embodiments, include luminal lateral groove 36 having chamfered proximal end 56, as shown in FIG. 5D. In such configurations, the luminal lateral grove 36 can be formed with a first radially extending (or "vertical" as depicted int eh figures) wall, connected to a longitudinally extending (or "horizontal") wall, which is in turn connected to an acutely angled "diagonally" extending third wall. FIG. 5B illustrates the configuration of the device when the grooves 36 and 18 (of dilator tip 28 and mounting component 12, respectively) are aligned with the circlip 42 positioned within these (aligned) grooves. FIG. 5D illustrates the configuration of the device when the grooves 36 and 18 (of dilator tip 28 and mounting component 12, respectively) are longitudinally offset with the circlip 42 positioned within only groove 18 of the mounting component 12.

Alternatively, luminal lateral groove 36 need not include a chamfered proximal end 56, but, rather, can be formed with a proximal end that is normal to luminal conduit 34, as shown in FIGS. 1A-1F. Luminal conduit 34 of dilator tip 28 includes threaded portion 66, whereby, when dilator tip 28 is mounted on mounting component 12, threaded portions 64,66 of mounting component 12 and dilator tip 28, respectively, are threadably engaged, as shown in FIGS. 5A and 5B. In this embodiment, dilator tip 28 does not rotate axially about longitudinal axis 22 relative to mounting component without either threading or unthreading dilator tip 28 onto, or off of, mounting component 12.

Assembly of dilator tip 28 on mounting component 12 includes axial rotation of mounting component 12 relative to dilator tip 28, whereby threaded portion 62 of mounting component 12 and threaded portion 66 of dilator tip 28 engage and cooperatively cause longitudinal movement relative to each other along longitudinal axis 22, whereby mounting component 12 travels longitudinally along luminal conduit 34 until circlip 42 engages chamfered proximal end 32 of luminal conduit 34, whereupon continued relative axial rotation of mounting component 12 relative to dilator tip 28 causes circlip 42 to travel longitudinally along chamfered surface 50 of chamfered proximal end 32 of dilator tip 28, as can be seen in FIGS. 5C and 5D, thereby radially compressing circlip 42 until it enters luminal lateral groove 36 of dilator tip 28, as shown in FIGS. 5A and 5B, thereby securing dilator tip 28 to mounting component 12.

In various embodiments, also shown in FIGS. 5A through 5D, chamfered luminal proximal end 56 of luminal lateral groove 36 is defined by luminal lateral chamfered proximal surface 58, whereby relative axial rotation of mounting component 12 and dilator tip 28 causes retraction of mounting component 12 relative to dilator tip 28, whereby circlip 42 travels longitudinally in proximal direction of arrow 60 across luminal chamfered proximal surface 58 of chamfered proximal end 56 of luminal lateral groove 36 until circlip 42 is sufficiently radially compressed to move longitudinally out of luminal lateral groove 36. With continued relative axial rotation of mounting component 12 relative to dilator tip 28, circlip 42 expands, and mounting component 12 retracts further from luminal conduit 34 of dilator tip 28 until dilator tip 28 and mounting component 12 are no longer threadably engaged, thereby releasing mounting component 12 from dilator tip 28 or, conversely, dismounting dilator tip 28 from mounting component 12.

Figures 6A, 6B:
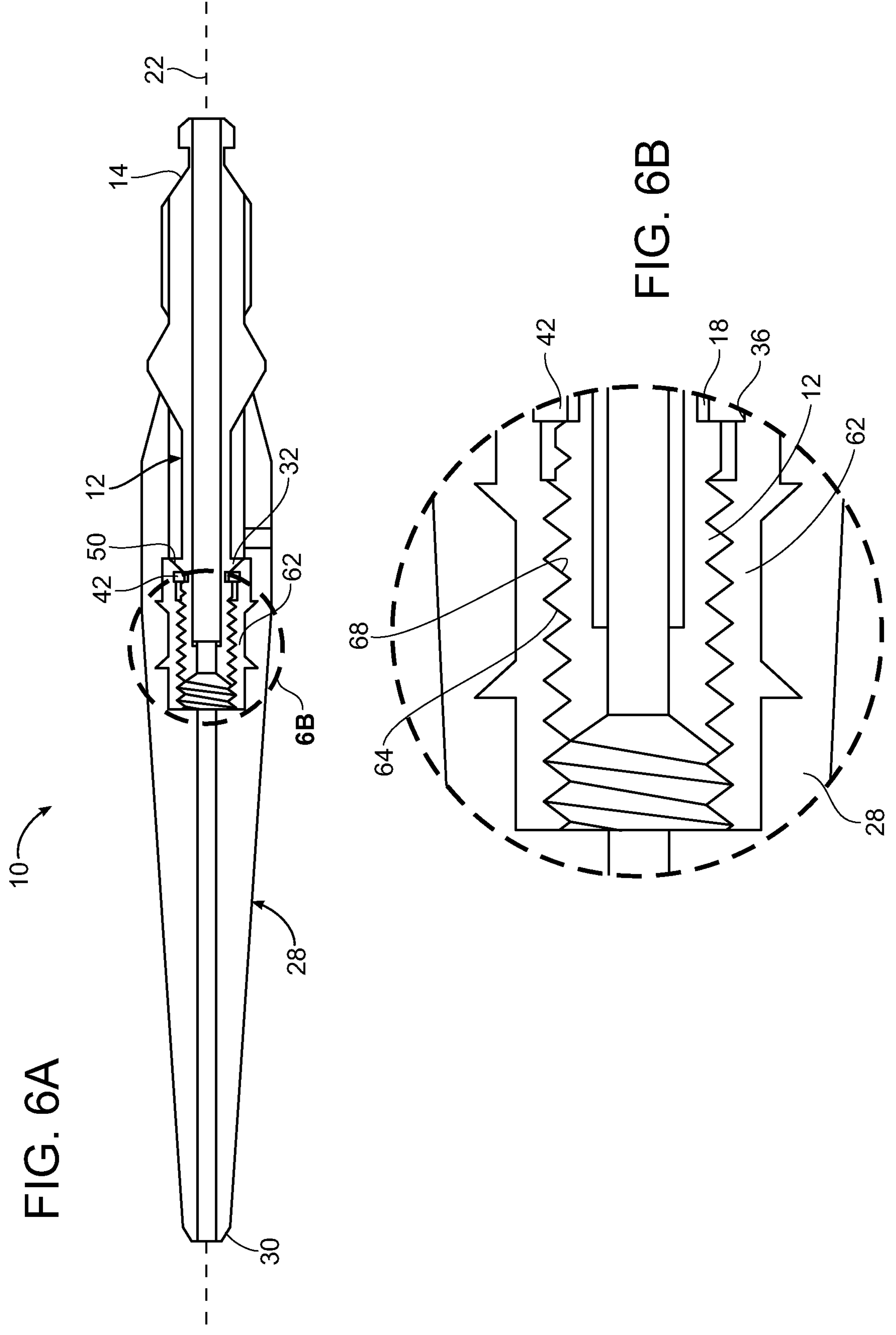
FIG. 6A is a cross-sectional view of yet another embodiment of the dilator tip assembly of the present disclosure, wherein the dilator tip includes an insert, and wherein the insert and the mounting component are threadably engaged.
FIG. 6B is a detail of the threaded engagement of the insert and the mounting component.

FIGS. 6A and 6B are cross-sectional representations of yet another embodiment of the dilator tip assembly of the present disclosure, wherein dilator tip 28 includes threaded insert 62. Threaded insert 62 is similar to insert 52 of FIGS. 4A-4F, but includes threaded portion 68. Dilator tip 28 of FIGS. 6A-6B is similar to that of dilator tip 28 of FIGS. 4A-4F, and the threads of dilator tip 28 match the threads of threaded portion 64 of mounting component 12. As in the other embodiments of this present disclosure, chamfered proximal end 32 of dilator tip 28 includes luminal conduit chamfered surface 50 to thereby cause radial compression of circlip 42 during progressive threaded engagement of threaded portions 64,68 of mounting component 12 and dilator tip 28, respectively, and during entry of mounting component 12 into luminal conduit 34 of dilator tip 28. Also, in one embodiment, as is also shown in FIGS. 4A-4F, described supra, the embodiment of FIGS. 6A-6B can include luminal lateral groove 36 that is chamfered at a proximal end to form chamfered luminal proximal end 56 defined by luminal lateral groove proximal chamfered surface 58, to thereby cause progressive radial compression of circlip 42 by axial rotation of mounting component 12 about longitudinal axis 22 relative to dilator tip 28 during unthreading and consequent retraction of mounting component 12 from dilator tip 28.

EQUIVALENTS

Those skilled in the art will recognize, and will be able to ascertain using no more than routine experimentation, many equivalents to the specific embodiments of the present disclosure described herein. Such equivalents are intended to be encompassed by the following claims.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A dilator tip assembly of an endoprosthetic delivery device, comprising:

a) a mounting component of an endoprosthetic delivery device, the mounting component including a proximal end and a distal end, and defining a mounting component lateral groove between the proximal end and the distal end;

b) a dilator tip of the endoprosthetic delivery device mountable on the distal end of the mounting component, the dilator tip having a proximal end and a distal end, and defining a luminal conduit having a chamfered proximal end, and wherein the luminal conduit includes a luminal lateral groove between the proximal end and the distal end of the luminal conduit; and c) a circlip that is mountable on the mounting component at the mounting component lateral groove, wherein longitudinal travel of the circlip, while mounted on the mounting component lateral groove, along the chamfered proximal end toward the luminal conduit causes radial compression of the circlip, whereby the circlip is directed to the luminal lateral groove and expands within the luminal groove, aligning with and engaging the luminal lateral groove, and securing the dilator tip to the mounting component, the dilator tip thereby being mounted on the mounting component.

2. The dilator tip assembly of claim 1, wherein the dilator tip is tapered at the distal end.

3. The dilator tip assembly of claim 2, wherein the circlip is an E-clip.

4. The dilator tip assembly of claim 3, wherein the E-clip includes at least 250 ksi 300 series stainless steel.

5. The dilator tip assembly of claim 1, wherein the luminal conduit extends through the dilator tip to the distal end of the dilator tip.

6. The dilator tip assembly of claim 1, wherein the luminal lateral groove defines a luminal chamfered proximal end and the dilator tip is removable from the mounting component by retraction of the mounting component from the luminal conduit to cause travel of the circlip along the luminal chamfered proximal end of the luminal lateral groove, thereby radially compressing the circlip and causing subsequent travel of the circlip from the luminal lateral groove and from the luminal conduit, and dismounting the dilator tip from the mounting component.

7. The dilator tip assembly of claim 6, wherein the dilator tip includes threads that define, at least in part, the luminal conduit.

8. The dilator tip assembly of claim 7, wherein the mounting component includes a threaded portion at the distal end that threadably engages the threads that define, at least in part, the luminal conduit, and the mounting component lateral groove is proximal to the threaded portion of the mounting component, whereby the mounting component can be removed from the dilator tip by axial rotation of either the mounting component or the dilator tip relative to each other to thereby disengage the threaded portion of the mounting component from the threads of the luminal conduit.

9. The dilator tip assembly of claim 7, wherein the dilator tip includes an insert that defines at least a portion of the threads that define, at least in part, the luminal conduit.

10. The dilator tip assembly of claim 9, wherein the mounting component includes a threaded portion at the distal end that threadably engages the threads of the luminal conduit, and the mounting component lateral groove is proximal to the threaded portion of the mounting component, whereby the mounting component can be removed from the dilator tip by axial rotation of either the mounting component or the dilator tip relative to each other to thereby disengage the threaded portion of the mounting component from the threads of the luminal conduit.

11. The dilator tip assembly of claim 9, wherein the chamfered proximal end of the luminal conduit is defined by the insert.

12. The dilator tip assembly of claim 1, wherein the dilator tip includes an aromatic ether-based thermoplastic polyurethane.

13. The dilator tip assembly of claim 1, further comprising an insert, wherein the insert includes at least one of 303 stainless steel and 17-4PH stainless steel.

14. The dilator tip assembly of claim 1, wherein the mounting component includes at least one of 303 stainless steel and polyether ether ketone.

15. A method of mounting a dilator tip on a mounting component of an endoprosthetic delivery device, comprising the steps of:

a) assembling a circlip with a mounting component of an endoprosthetic delivery device at a mounting component lateral groove defined by the mounting component and located between a proximal end and a distal end of the mounting component; and b) directing the distal end of the mounting component, while assembled with the circlip, into a chamfered proximal end of a luminal conduit of a dilator tip of the endoprosthetic delivery device, whereby the circlip is radially compressed during travel in a distal direction along the chamfered proximal end, further travel of the circlip into the luminal conduit of the dilator causing the circlip to be directed to and radially expand within a luminal groove defined by the luminal conduit, thereby mounting the dilator tip on the mounting component.

16. The method of claim 15, further including the step of retracting the mounting component from the luminal conduit, whereby the circlip is compressed by longitudinal travel along a chamfered proximal end of the luminal groove of the dilator tip, and subsequent travel of the circlip along the luminal conduit and from the luminal conduit causes the dilator tip to dismount from the mounting component.

17. The method of claim 15, wherein the mounting component and the luminal conduit of the dilator tip each define a threaded portion, wherein the threaded portions of the mounting component and the dilator tip are threadably engaged when the dilator tip is mounted on the mounting component, and whereby selective axial rotation of the dilator tip relative to the mounting component relative to each other and about a longitudinal axis causes progressive entry or retraction of the mounting component from the luminal conduit of the dilator component.

18. The method of claim 15, wherein the luminal groove defined by the luminal conduit of the dilator component defines a luminal proximal end.

* * * * *